(12) United States Patent
Cremaschi et al.

(10) Patent No.: US 7,235,522 B2
(45) Date of Patent: Jun. 26, 2007

(54) USE OF MICROPARTICLES HAVING A PROTEIN AND AN ANTIBODY ADSORBED THEREON FOR PREPARING A PHARMACEUTICAL COMPOSITION FOR INTRANASAL ADMINISTRATION

(75) Inventors: Dario Cremaschi, Milan (IT); Cristina Porta, Milan (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 706 days.

(21) Appl. No.: 09/988,150

(22) Filed: Nov. 19, 2001

(65) Prior Publication Data

US 2002/0058069 A1    May 16, 2002

Related U.S. Application Data

(63) Continuation of application No. 09/402,474, filed as application No. PCT/EP98/02214 on Apr. 8, 1998, now abandoned.

(30) Foreign Application Priority Data

Apr. 14, 1997  (IT) ............................... MI97A0856

(51) Int. Cl.
*A61K 38/00*    (2006.01)
*A61K 39/395*   (2006.01)

(52) U.S. Cl. ........................................ 514/2; 424/130.1
(58) Field of Classification Search ............. 424/178.1, 424/130.1, 134.1, 489, 491
See application file for complete search history.

(56) References Cited

U.S. PATENT DOCUMENTS 5,879,712 A * 3/1999 Bomberger et al. ......... 424/489

FOREIGN PATENT DOCUMENTS

| EP | 0 474 453 | 3/1992 |
| WO | 94 28879 | 12/1994 |
| WO | WO 94/28879 A1 * | 12/1994 |

OTHER PUBLICATIONS

Almeida et al. "Nasal Delivery of Vaccines", Jnl. of Drug Targeting, 1996, vol. 3, pp. 455-467.*
Smith et al. Experimental Physiology, 1995, vol. 80, pp. 735-743.*
Spit et al, Jan. 1989. "Cell and Tissue Research". Abstract only.
K. Raehenbuhl et al, Feb. 1997, "Behring Institute Mitteilungen" Abstract only.

* cited by examiner

*Primary Examiner*—Misook Yu
(74) *Attorney, Agent, or Firm*—Oblon, Spivak, McClelland, Maier & Neustadt, P.C.

(57) ABSTRACT

Use of microparticles having a protein and an antibody adsorbed thereon for preparing a pharmaceutical composition for intranasal administration.

8 Claims, No Drawings

USE OF MICROPARTICLES HAVING A PROTEIN AND AN ANTIBODY ADSORBED THEREON FOR PREPARING A PHARMACEUTICAL COMPOSITION FOR INTRANASAL ADMINISTRATION

The present application is a Continuation Application of U.S. Ser. No. 09/402,474 filed Nov. 18, 1999 now abandoned, which in turn is a National Stage Application under 35 U.S.C. § 371 of PCT/EP98/02214 filed Apr. 8, 1998.

The present invention relates to use of a microparticle having a protein and an antibody adsorbed thereon for preparing a pharmaceutical composition for intranasal administration.

In the present description and the following claims, the term "protein" comprises any compound of condensation of two or more amino acids. The term therefore comprises, but is not limited to, biologically active peptides, polypeptides and proteins.

It is known that in various animal species, including human beings, absorption of proteins administered by nasal route is higher than 40% for peptides having from 3 to 6 amino acids (AA), about 10-15% for polypeptides having from 9 to 27 AA, and less than 1% for polypeptides having greater molecular weight (for example, for insulin (51 AA), the absorption is almost zero), although there are appreciable differences for the same peptide from species to species, or even from individual to individual of the same species [Lee W. A., Longenecker J. P. "Biopharm. Manufact." April pp 1-7 (1988)].

This is why at the end of the 80s only 3 nonapeptides, as such, (desmopressin, lypressin, oxytocin) were administered by the nasal route, and protease inhibitors and enhancers of transit through the nasal mucous membrane were studied from the early 80s. Generally, these enhancers are surfactants which increase passive permeability of nasal mucous membrane. Due to which it has been possible to have formulations for intranasal administration of calcitonin (32 AA), insulin (51 AA), growth hormone (191 AA) and other proteins and high molecular weight polypeptides [Lee W. A., Longenecker J. P. "Biopharm. Manufact." April pp. 1-7 (1988); Verhoef J. C. et al. "Eur. J. of Drug Metab. and Pharmacokin." 15, 83 (1990); Mishima M. et al. "J. Pharmacobio-Dyn." 10, s.69 (1987); Mishima M. et al. "J. Pharmacobio-Dyn." 12 32 (1989); Watanabe Y et al. "Chem. Pharm. Bull." 40, 3100 (1992); Schipper N. G. M. et al "Pharmaceutical Res. 10, 682 (1993); Shao Z. et al. "Pharmaceutical Res." 11, 1174 (1994)].

The enhancers, however, since they are essentially surfactants, have the disadvantage of damaging mucous membrane more or less profoundly and reversibly, thus increasing the passive permeability of the same.

In order to attempt to favour absorption, nasal transit retarders have also been used, such as viscous agents, adhesive polymers, and the like, and the results obtained have been moderate. Retardants, however, also have toxic effects on mucous membrane and cilia.

To obviate these disadvantages, administration of drugs incorporated in microspheres of starch which are not absorbed because they are too large but which are partially hydrated in the nasal lumen and slowly release the previously incorporated peptides has been proposed [Illum L. et al. "Int. J. Pharm." 39, 189 (1987); Björk E., Edman P. "Int. J. Pharm." 47, 233 (1988)]. In this manner a retarding effect was obtained together with an improvement of absorption of small and medium-sized molecules. However, the absorption of large molecules does not improve because the mucous membrane is not impaired.

Finally, PCT patent application WO 94/28879 discloses a pharmaceutical composition for oral administration comprising a biologically active material, an antibody which specifically binds to the said biologically active material and a plurality of microparticles of polymeric material. In particular, the biologically active material belongs to the family of the peptides, polypeptides and proteins. Preferably, the microparticles are microspheres of polystyrene.

The biologically active material and antibodies are adsorbed on the said microparticles and the latter are endocytosed by the epithelium coating the follicles of the Peyer's patches in the mouse. It is therefore possible to calculate in the laboratory animal both the quantity of microparticles entering the carrier cells (uptake) and the quantity of microparticles which effectively passes transmurally and reaches the lymph in the mesenteric duct, which collects all the transported material.

In the above-mentioned application, the most efficient transport has been obtained by using bovine growth hormone as the protein and the specific antibody of the same, bGH-Ab, as the antibody.

Uptake measurements were carried out by inserting in vivo in the jejunum and ileum of the rat $3.6 \times 10^{11}$ coated microparticles, fixing the tissue after 90 minutes and carrying out measurement (6 endocytotic cycles in 90 minutes were taken into consideration in the calculation).

The results obtained were as follows:
a) total uptake in 90 minutes through 40 cm$^2$: 8,400,000 microparticles [yield=0.023°/oo (=8,400,000/3.6×10$^{11}$)];
b) total uptake per unit of area in 90 minutes through 40 cm$^2$: 210,000 microparticles/cm$^2$; [yield/cm$^2$=0.00058°/oo (=210,000/3.6×10$^{11}$).

In turn, transmural flow measurements were carried out by inserting in vivo in the jejunum+ileum of the rat $3.6 \times 10^{11}$ coated microparticles and collecting the lymph from the cannulated mesenteric duct every 5 minutes.

The results were as follows:
a) transmural transport on 40 cm$^2$ in 90 minutes: 65,000 microparticles: [yield on 40 cm$^2$=65,000/3.6×10$^{11}$ (=0.00018°/oo)];
b) material transported transmurally in 90 minutes/cm$^2$: 1625 microparticles/cm$^2$; [yield/cm$^2$=4.4×10$^{-9}$ (=0.0000044°/oo)].

These data show that yield of endocytosis in the intestine is 130 times (2.3×10$^{-5}$/1.8×10$^{-7}$) higher than yield of transmural transport. This means that out of 130 endocytosed particles, 129 remain trapped in the said lymphoid tissue of the Peyer's patches and only 1 passes into the lymph.

It has now surprisingly been found that yield of active transport in nasal mucous membrane of a protein and the specific antibody of the said substance adsorbed on microparticles of polymeric substance is 400 thousand times higher than that of the intestine.

More particularly, since the absorption data in experiments on the intestine were obtained in vivo, these data relate to an incoming flow (lumen-lymph) comprising both active and passive paracellular transport which increases yield. Based on this initial premise, the ratio of yield of nasal and intestinal transport is without doubt higher than the previously mentioned 400 thousand times.

In fact, nasal mucous membrane was studied isolated in vitro, and it was possible to measure the two opposite, unidirectional flows of coated microparticles, and net absorption was calculated as the difference of these flows. Net absorption of nasal mucous membrane therefore does not include the incoming passive component but, unlike what has been reported for the intestine, is solely the result of active absorption.

It is further worth noting that, in addition to the extremely favourable yield ratio, in general the nasal route is also more advantageous in comparison with the oral route in that the absorbed substance does not have to pass through the taxing digestive system of the gastrointestinal tract and having then entered the circulation it does not suddenly have to pass through the liver.

Therefore, it is a first object of the present invention to provide an use of a polymeric of a microparticle having a protein and an antibody adsorbed thereon for preparing a pharmaceutical composition for intranasal administration.

The protein is preferably selected from the group comprising BSA (bovine serum albumin), insulin, enkephalin, hormones, growth factors, cytokines, coagulation factors, neuropeptides, antimicrobial agents and fragments thereof. The antibody, in turn, is an immunoglobulin selected from the group comprising IgM, IgA and IgG. The immunoglobulin is preferably specific for the protein. The microparticles preferably are microspheres of non-immunogenic polymeric materials such as polystyrene, latex or other polymers. Optionally, the polymeric material is of biodegradable type.

Preferably, the pharmaceutical composition according to the present invention is prepared in a suitable dosage form comprising an effective dose of a protein and an antibody adsorbed on microparticles of polymeric material together with a pharmaceutically acceptable inert ingredient.

Examples of suitable dosage forms for administration by the intranasal route are creams, ointments, aerosols, sprays and drops.

The dosage forms may also contain other conventional ingredients such as preservatives, stabilisers, buffers, salts for adjusting the osmotic pressure, emulsifiers, flavourings, and the like.

The quantity of protein and antibody in the pharmaceutical composition according to the present invention may vary within a wide range in relation to known factors such as, e.g., the stage and seriousness of the disease, the patient's body weight, the number of daily doses and the activity of the selected protein. The optimum quantity can nevertheless easily and routinely be determined by a person skilled in the art.

Generally, the protein/immunoglobulin ratio is of from 1 to 15,000 mols of protein for each mole of immunoglobulin. Preferably of from 1 to 5,000, even more preferably of from 1 to 100 mols of protein for each mole of immunoglobulin.

In turn, the quantity by weight of protein in the pharmaceutical composition according to the present invention will be easily determined in the individual case by a person skilled in the art on the basis of the known activity of the protein used.

The dosage forms of the pharmaceutical composition according to the present invention may be prepared by methods well known to the pharmaceutical chemist comprising mixing, granulation, compression, dissolution, sterilization, and the like.

The activity of the proteins adsorbed on the microparticles together with antibodies specific for the protein under evaluation has been assessed by means of the experiments described below.

EXAMPLE 1

Transport of Microparticles by Intranasal Route

Two heterolateral nasal mucous membranes isolated from New Zealand albino male rabbits (body weight: 3-3.5 kg) were used for the experiment, after sacrifice by cervical dislocation. The areas of mucous membrane corresponding to the concha nasalis superior were washed with Krebs-Henseleit solution ["Comp. Biochem. Physiol.", Cremaschi D. et al., 99A, 361, (1991); "Biochem. Biophys. Acta", Cremaschi D. et al., 27, 1280 (1996)] and then mounted in teflon in Ussing chamber (exposed area 0.3 cm$^2$) and incubated with Krebs-Henseleit solution, maintained at 27±1° C.

The composition of the Krebs-Henseleit solution was as follows (in mM): Na$^+$142.9; K$^+$5.9; Ca$^{2+}$2.5; Mg$^{2+}$1.2; Cl$^{31}$ 127.7; HCO$_3$$^{31}$ 24.9; H$_2$PO$_4$_1.2; SO$_4$$^{2-}$1.2; glucose 5.5. The pH was maintained at 7.4 whilst washing through with O$_2$95% +CO$_2$5%. The washing gas was also used to oxygenate the tissue and mix the solution.

Differences of transepithelial electric potential (V$_{ms}$) were determined on the thus mounted heterolateral tissues, using a digital multimeter (Keithley Instr., Cleveland, USA, model 136). Measurements were made every 10 minutes during the first 30 minutes of the experiment (to enable assessment of functionality of the epithelium following isolation), and at the end of the experiment (150 minutes after the start; i.e. a 120 minute incubation period).

At the end of the pre-incubation period, the solution from the submucosal side of one of the two tissues and from the mucosal side of the other tissue was substituted by 250 μl of a suspension of fluorescent polystyrene microspheres (conjugated with fluorescein isothiocyanate, FITC: Polyscience Inc., Warrington, Pa., USA) approximately 0.5 μm of diameter. The concentration of the microspheres was measured on 10 μl samples (taken at least at the start and end of the incubation period), with straight lines of absorbency calibration (λ5 photometer available from Perkin-Elmer Corp., Norwalk, Conn., USA) at 600 nm wavelength. The reference concentrations for the microspheres were predetermined in a Burker chamber after suitable dilution (Orthoplan MPV2 fluorescence microscope by Leitz GMBH, D-6330 Wetzlar, Germany). During the experiment the initial and final concentrations of the microparticles showed no significant changes. These microparticles transported during the 120 minutes of incubation were measured in the Burker chamber because of their low concentration and expressed as unidirectional mucosa-submucosa flows (J$_{ms}$) or vice-versa (J$_{sm}$) in number of microparticles cm$^{-2}$h$^{-1}$.

Both the donor solution and the solution containing the transported microparticles were subjected to ultrasound at the start and end of the experiment, prior to carrying out measurements, in order to prevent the microparticles placed in Krebs-Henseleit from aggregating with each other and tending to be absorbed in the tissue. The donor solution was completely renewed every 30 minutes, this procedure having proved adequate to maintain a constant concentration of free microparticles.

EXAMPLE 2

Transport by Intranasal Route of Proteins Adsorbed on Microparticles

The same procedure was carried out as in the previous Example 1, except that the microparticles were suspended in a proteic solution (6.5.10$^{-6}$ M) and the complete suspension was incubated for 90 minutes at 37° C. 4 washes were then carried out, each consisting of precipitation by centrifugation and re-suspension in Krebs-Henseleit solution containing bovine serum albumin, BSA ($7.4.10^{-4}$ M, 5% p/v).

EXAMPLE 3

Transport by Intranasal Route of Antibodies Adsorbed on Microparticles

The same procedure was followed as in the previous Examples 1 and 2, except that the microparticles were suspended in a proteic solution consisting of an antibody.

EXAMPLE 4

Transport by Intranasal Route of Adsorbed Proteins Bound to Antibodies on Microparticles The same procedure was carried out as described in the previous Examples 1 and 2, except that polypeptides adsorbed on microparticles and specifically bound to antibodies were used. The microparticles were first of all suspended in a suitable proteic solution ($6.5.10^{-6}$ M) and the whole suspension was incubated for 90 minutes at 37° C. 4 washes were then carried out, each consisting of precipitation by centrifugation and re-suspension in Krebs-Henseleit solution containing BSA ($7.4.10^{-4}$ M, 5% p/v). Finally, a second incubation of the microparticles coated with a solution containing a specific anti-polypeptide antibody was carried out ($6.5.10^{-8}$ M) for 16 hours at 4° C.

For the study of the kinetics of transport of the coated microparticles, the latter were not diluted or concentrated until after they had been coated in the usual initial concentration, such that homogeneous coatings were present irrespective of the final concentration of microparticles.

Among the polypeptides used, the bovine serum albumin (BSA), immunoglobulin A (human colostrum IgA), the immunoglobulin G (murine anti-human insulin and anti-BSA) had been supplied by Sigma (St. Louis, Mo., USA), whilst bovine insulin and the enkephalin ([Leu5]enkephalin) had been supplied by Calbiochem AG (Lucerne, Switzerland).

The results of Examples 1-4 are illustrated in Table 1, showing mucosa-submucosa flows ($J_{ms}$) and vice-versa ($J_{sm}$) of native microparticles (not coated) or coated with various proteins.

Irrespective of the type of coating, the experiment was only considered valid when the isolated mucous membrane was found to be vital both at the start of the experiment and during pre-incubation as well as at the end of incubation. The parameter taken into consideration for this purpose was the difference of transepithelial electric potential ($V_{ms}$), the indices of both transepithelial transport of active electrogenic ions and cell metabolism (which supports the latter) and of the integrity of the epithelium as a barrier.

Initial minimum $V_{ms}$ was +1 mV (positive submucosa). $V_{ms}$ increased slowly and progressively during the experiment, thus indicating not only that the isolated mucous membrane was not undergoing degradation, but also indicating a constant recovery of functionality of the said mucous membrane in vitro. The trend in time proved to be similar to that reported by Cremaschi D. et al. "Comp. Biochem. Physiol." 99A, 361, (1991).

The incubation temperature was 27±1° C. As compared with 37° C., this temperature lowers metabolism and transport approximately twice as much, but renders the isolated tissue more stable. In the various types of experiments carried out, mean $V_{ms}$ after 30 minutes of pre-incubation at 27° C. (before insertion of the donor solution with the microparticles and start of incubation with flow measurements) was 40±0.1 mV (134 mucosae).

$V_{ms}$ at the end of the 120 minutes of incubation was 6.6±0.2 mV (134 mucosae, p<0.01).

Irrespective of the type of coating, concentration of microparticles in the donor solutions showed no significant reduction in time during the 120 minutes of incubation. This concentration, in fact, was equal to $3.25\pm0.05\times10^{11}$ microparticles/ml (134 experiments) at the start of incubation and $3.22\pm0.04\times10^{11}$ microparticles/ml (134 experiments carried out by us) at the end of incubation.

This means that flows $J_{ms}$ and $J_{sm}$ were unidirectional in the period of time considered and that no losses of microparticles occurred due to absorption or aggregation. This furthermore gave us a safe reference for concentration of the solution creating the flows.

The results reported in Table 1 show that:

a) in the different conditions of coating, $J_{sm}$ values correspond to approximately 3-6 million microparticles $cm^{-2}h^{-1}$ out of the 325 billion microparticles/ml of the donor solution;

b) when the microparticles are not coated with polypeptides, $J_{ms}$ value is not significantly different from $J_{sm}$ value; therefore, no net absorption of microspheres occurs ($J_{net}$ not significantly different from zero);

c) coating with polypeptides, irrespective of the polypeptide used (BSA, insulin, enkephalin, IgA, anti-insulin IgG, anti-BSA IgG) causes $J_{ms}$ value always to be significantly higher than $J_{sm}$ value; therefore net absorption occurs ($J_{net}$ significantly different from zero);

d) when, after coating of the microparticles via adsorption of insulin or BSA, the respective antibody (anti-insulin IgG or anti-BSA IgG in a concentration of 1:100 with respect to the concentration used for adsorption) is bound to them with a bond which is specific for these two proteins, $J_{ms}$ is strongly stimulated both in respect of that of insulin and that of BSA, as well as in respect of that of the two antibodies aspecifically adsorbed on the microparticles; consequently, net absorption ($J_{net}$) shows a notable increase.

Since the highest net flows were obtained with insulin bound to its specific IgG, the kinetics of transport were examined for this type of coating. To this end, the microparticles were coated as previously disclosed, then diluted or concentrated, and the flows measured in different concentrations of microparticles.

Table 2 shows the results obtained carrying out 6 experiments per each concentration. These results show that:

a) with a concentration of 2 billion and 200 million microparticles/ml, $J_{ms}$ is not significantly different from $J_{sm}$. $J_{net}$ is therefore not different from zero;

b) with higher concentrations, whilst $J_{sm}$ shows no statistically significant change, $J_{ms}$ becomes significantly higher than $J_{sm}$. $J_{net}$ is therefore statistically different from zero;

c) with increased concentration, $J_{ms}$ increases progressively and the difference from $J_{sm}$ also increases; $J_{net}$ consequently also increases. An increase is still observed at a concentration of 982 billion microparticles/ml, i.e. 500 times greater than the minimum concentration used;

d) the trend of kinetics is sigmoid and maximum yield/$cm^2$ of transepithelial transport is obtained with $3.2\times10^{11}$ microparticles/ml, that is equivalent to 1.7°/oo. This yield, obtained at 27° C., is 400,000 times greater than the corresponding yield obtained in the intestine, measured at 37° C. and considering as flow the total of active net flow and passive lumen-lymph flow, as already said ($1.7\times10^{-3}/4.4\times10^{-9}$=400,000).

TABLE 1

Flows of native microparticles or microparticles coated with a polypeptide (Ag) or with an antibody or with a polypeptide bounded to the specific IgG thereof (Ag + Ab).

| Microparticles coating | Number of Experiments | $V_{ms}$ (mV) initial | $V_{ms}$ (mV) final | Concentration ($10^{11}$/ml) initial | Concentration ($10^{11}$/ml) final | Flows ($10^6$ cm$^{-2}$h$^{-1}$) $J_{ms}$ | Flows ($10^6$ cm$^{-2}$h$^{-1}$) $J_{sm}$ | Flows ($10^6$ cm$^{-2}$h$^{-1}$) $J_{net}$ |
|---|---|---|---|---|---|---|---|---|
| not coated (native) | 5 | 4.4 ± 0.5 (10) | 6.2 ± 0.4** (10) | 2.53 ± 0.06 (10) | 2.47 ± 0.02 (10) | 3.94 ± 0.48 | 3.37 ± 0.44 | 0.5 ± 0.38 |
| BSA | 6 | 5.0 ± 0.4 (12) | 7.6 ± 0.4** (12) | 3.45 ± 0.05 (12) | 3.54 ± 0.05 (12) | 7.46 ± 0.64•• | 4.85 ± 0.23 | 2.60 ± 0.50°° |
| Insulin | 13 | 3.1 ± 0.3 (26) | 5.2 ± 0.3** (26) | 3.81 ± 0.08 (26) | 3.72 ± 0.11 (26) | 11.06 ± 1.47•• | 3.96 ± 0.57 | 7.10 ± 1.15°° |
| Enkephalin | 6 | 4.0 ± 0.3 (12) | 7.2 ± 1.1** (12) | 3.20 ± 0.05 (12) | 3.28 ± 0.06 (12) | 7.26 ± 0.53•• | 4.66 ± 0.09 | 2.60 ± 0.53°° |
| IgA | 6 | 3.5 ± 0.4 (12) | 6.8 ± 1.0** (12) | 3.26 ± 0.13 (12) | 3.18 ± 0.9 (12) | 6.98 ± 0.83• | 3.92 ± 0.16 | 3.06 ± 0.87° |
| IgG anti-insulin | 6 | 3.0 ± 0.2 (12) | 7.1 ± 0.5** (12) | 2.78 ± 0.10 (12) | 2.80 ± 0.10 (12) | 13.47 ± 1.08•• | 3.66 ± 0.22 | 9.81 ± 1.08°° |
| IgG anti-BSA | 6 | 5.7 ± 0.7 (12) | 9.0 ± 1.2** (12) | 3.23 ± 0.04 (12) | 3.34 ± 0.05 (12) | 10.15 ± 1.24•• | 4.08 ± 0.34 | 6.06 ± 0.94°° |
| Insulin + IgG anti-insulin | 13 | 3.3 ± 0.2 (26) | 5.4 ± 0.3** (26) | 3.17 ± 0.05 (26) | 3.01 ± 0.05 (26) | 74.23 ± 7.06•• | 5.91 ± 0.48 | 68.32 ± 6.87°° |
| BSA + IgG anti-BSA | 6 | 5.5 ± 1.0 (12) | 8.2 ± 0.8* (12) | 3.12 ± 0.07 (12) | 3.22 ± 0.08 (12) | 13.56 ± 1.49•• | 4.17 ± 0.31 | 9.39 ± 1.28°° |
| Means | | 4.0 ± 0.1 (134) | 6.6 ± 0.2** (134) | 3.25 ± 0.05 (134) | 3.22 ± 0.04 (134) | | | |

*,**p < 0.05 or 0.01 with respect to the initial value
°,°°p < 0.05 or 0.01 with respect to zero
•,••p < 0.05 or 0.01 with respect to $J_{sm}$

TABLE 2

Flows of microparticles coated with insulin bounded to anti-insulin IgG. Donor solution having different concentrations of microparticles.

| Microparticles concentration ($10^{11}$/ml) | Flows ($10^6$ cm$^{-2}$ h$^{-1}$) $J_{ms}$ | $J_{sm}$ | $J_{net}$ |
|---|---|---|---|
| 0.022 ± 0.002 | 5.84 ± 0.65 | 5.14 ± 0.54 | 0.69 ± 0.44 |
| 0.14 ± 0.01 | 7.62 ± 0.55•• | 5.17 ± 0.35 | 2.45 ± 0.36°° |
| 0.32 ± 0.01 | 9.40 ± 0.78•• | 4.28 ± 0.12 | 5.12 ± 0.79°° |
| 0.69 ± 0.03 | 13.16 ± 0.69•• | 4.20 ± 0.18 | 8.96 ± 0.67°° |
| 1.52 ± 0.06 | 26.75 ± 1.43•• | 4.69 ± 0.21 | 22.06 ± 1.33°° |
| 1.73 ± 0.03 | 34.27 ± 1.66•• | 4.36 ± 0.16 | 29.91 ± 1.53°° |
| 2.79 ± 0.08 | 61.39 ± 3.87•• | 4.45 ± 0.34 | 56.94 ± 3.76°° |
| 5.43 ± 0.13 | 79.85 ± 5.73•• | 5.54 ± 0.63 | 74.32 ± 5.81°° |
| 9.82 ± 0.14 | 98.84 ± 7.12•• | 6.31 ± 0.90 | 92.53 ± 6.67°° |

°°p < 0.01 with respect to zero
••p < 0.01 with respect to $J_{sm}$

The invention claimed is:

1. A method for intranasally administering a composition comprising a microparticle and an antibody adsorbed thereon, wherein said administering comprises having a protein and an antibody thereon with the nasal mucosa of a patient in need thereof, and wherein the transepithelial transport obtained with $3.2 \times 10^{11}$ microparticles/ml is 1.7%, wherein said antibody is an immunoglobulin specific for the protein.

2. The method of claim 1, wherein said protein is selected from the group consisting of BSA, insulin, enkephalin, hormones, growth factors, cytokines, coagulation factors, antimicrobial agents.

3. The method of claim 1, wherein said antibody is an immunoglobulin selected from the group consisting of IgM, IgA, and IgG.

4. The method of claim 1, wherein said microparticle is biodegradable.

5. The method of claim 1, wherein said microparticle comprises polystyrene.

6. The method of claim 1, wherein the ratio of protein to antibody is 1 to 15,000 moles of protein per mole of antibody.

7. The method of claim 1, wherein the ratio of protein to antibody is 1 to 5,000 moles of protein per mole of antibody.

8. The method of claim 1, wherein the ratio of protein to antibody is 1 to 100 moles of protein per mole of antibody.

* * * * *